United States Patent [19]

Reinicke

[11] Patent Number: 4,482,346
[45] Date of Patent: Nov. 13, 1984

[54] APPARATUS FOR INFUSING MEDICATION INTO THE BODY

[75] Inventor: Robert H. Reinicke, Mission Viejo, Calif.

[73] Assignee: Consolidated Controls Corporation, El Segundo, Calif.

[21] Appl. No.: 404,345

[22] Filed: Jul. 30, 1982

[51] Int. Cl.³ .............................................. A61M 5/00
[52] U.S. Cl. ........................... 604/152; 128/DIG. 12; 417/240; 417/417
[58] Field of Search ............... 417/240, 413, 416, 417, 417/540; 128/DIG. 12; 604/131, 151-153, 891

[56] References Cited

U.S. PATENT DOCUMENTS

| | | | |
|---|---|---|---|
| 3,559,644 | 2/1971 | Stoft et al. | 604/123 |
| 3,751,188 | 8/1973 | Willinger et al. | 417/240 |
| 4,193,397 | 3/1980 | Tucker et al. | 604/93 X |
| 4,209,014 | 6/1980 | Sefton | 604/152 X |
| 4,274,407 | 6/1981 | Scarlett | 604/153 |

Primary Examiner—Dalton L. Truluck
Attorney, Agent, or Firm—Mason, Kolehmainen, Rathburn & Wyss

[57] ABSTRACT

An integral valve and pumping unit is provided for infusing medication into the body which employs only one moving part. This pumping unit is connected to the medication supply reservoir through a first flow restriction device which has no moving parts but has directional flow characteristics so that liquid medication can flow readily from the reservoir to the pumping unit but flow from the pumping unit to the reservoir encounters a relatively high resistance. A second flow restriction device is connected between the pumping unit and the outlet catheter which is employed to infuse medication into the body, this second flow restriction device likewise having no moving parts and offering relatively little resistance to liquid flow from the pumping unit to the catheter while having relatively high resistance to flow in the opposite direction. The valve portion of the integral valve-pump unit ensures that no liquid can flow either from the reservoir to the catheter or vice versa, when the pumping unit is inoperative or when the reservoir is being filled.

36 Claims, 6 Drawing Figures

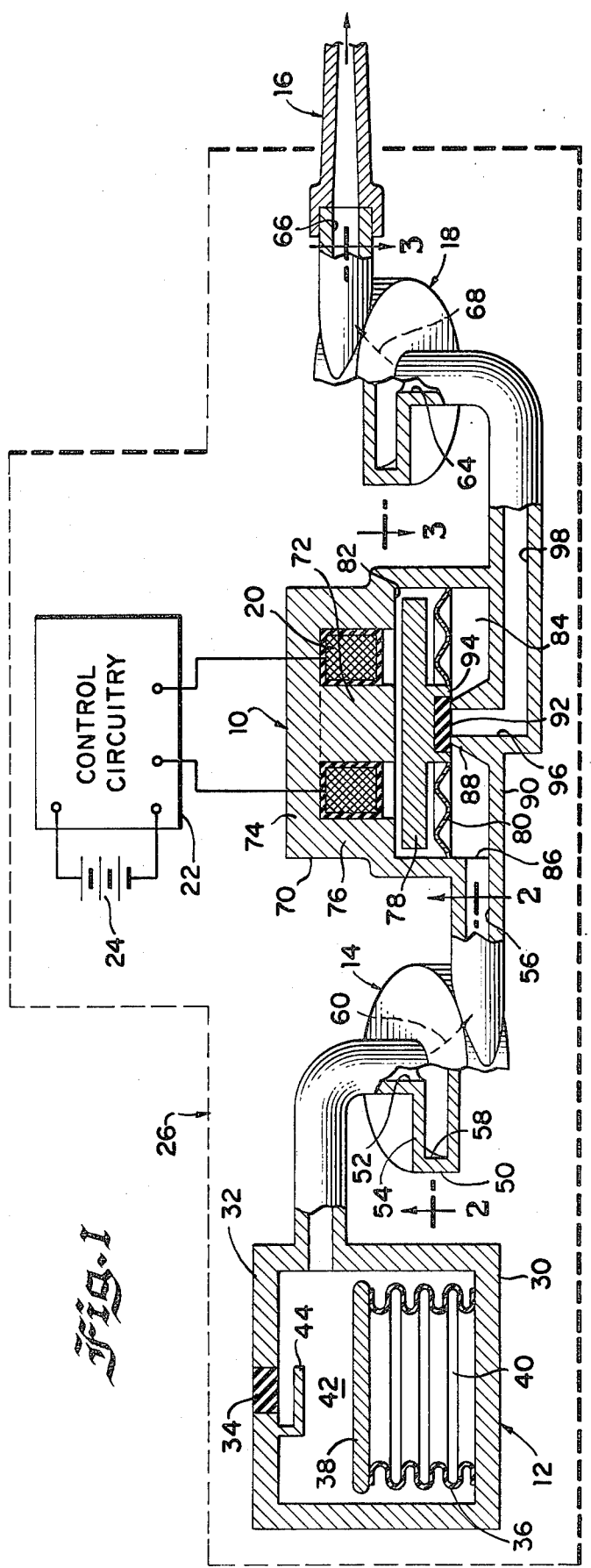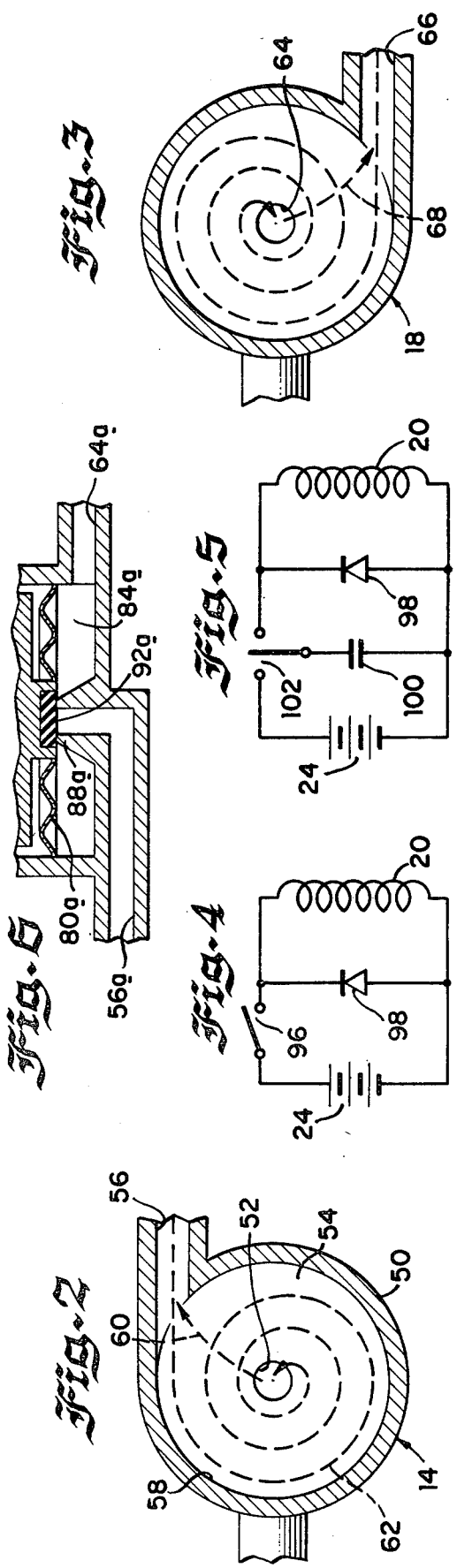

APPARATUS FOR INFUSING MEDICATION INTO THE BODY

BACKGROUND OF THE INVENTION

1. Field of the Invention

The present invention relates to apparatus for infusing medication, such as insulin, into human or animal bodies, such apparatus including a supply reservoir for the medication and an arrangement for infusing the medication into the body by means of a controllable dosing device for producing a desired rate of infusion.

2. Description of the Prior Art

Patients confined to bed can receive continuous infusion of a desired medication such as insulin, usually by a gravity fed system, having the flexibility to adjust the infusion rate, including the ability to start and stop infusion. Continuous, variable rate infusion (either subcutaneous or intravenous) has proven to offer benefits as compared to periodic injection by syringe.

Portable drug infusion devices are in use today that are worn externally by ambulatory patients for subcutaneous infusion. Some external devices allow the patients to adjust the infusion rate. Additionally, some external devices provide an automatically varied infusion rate. For example, a lower rate at night and a higher rate during the daytime may be provided by using electronic controls.

Prior art arrangements have also provided infusion devices that can be entirely implanted within the human body. This permits normal mobility without concern or any hindrance of an external device. Most of these devices provide a continous infusion at a pre-established flow rate. The potency of the drug being administered can be changed, however, to change the infusion characteristics. This requires penetration of the body by a syringe to withdraw any residual drug in the implanted device and then refilling the device with a drug of different potency. Such prior art implant arrangements are shown in Blackshear et al U.S. Pat. No. 3,731,681, Tucker et al U.S. Pat. No. 3,951,147, Tucker et al U.S. Pat. No. 4,193,397 and Tucker U.S. Pat. No. 4,221,219. Other prior art arrangements have utilized electronically controlled implanted medication infusion devices that automatically change the infusion flow rate as a function of the time of day in response to a computer program. Some of these devices allow noninvasive, temporary modifications of the infusion rate. For example, the device may be signaled by external action to infuse an increased amount of liquid. This can be done mechanically or by non-mechanical means such as telemetry. Some devices can also be reprogrammed by non-invasive techniques such as telemetry. Such programmable arrangements are shown, for example, in Haerton et al U.S. Pat. No. 4,077,045 and Ellinwood, Jr. U.S. Pat. Nos. 3,692,027, 3,923,060 and 4,146,029.

Prior art drug infusion devices can fail in various ways which could cause excessive and possibly lethal drug infusion. For example, drug reservoirs that are pressurized above body pressure can have a structural failure that allows the drug to leak into the body, in the case of implanted devices. If a valve is used to meter drug infusion from the outlet of an external or implanted pressurized drug reservoir device, excessive valve seat (internal) leakage or a valve "fail-open" (by sticking or other mechanical failure) will allow excessive infusion, possibly enough to be lethal.

In order to avoid the possibility of a lethal drug infusion, small pumps have been connected to drug reservoirs that have a pressure slightly less than body pressure. This greatly reduces the possibility of a structural failure in the reservoir causing a lethal drug infusion. For example, a crack in the reservoir results simply in body fluids leaking into the reservoir. However, these pumps introduce other problems. For example, when peristaltic pumps are employed, they are inefficient and batteries which power such peristaltic pumps must be replaced often which requires an operation on the patient. Also, peristaltic pumps must use plastic or elastomer tubes which allow the drug vapors to permeate into the electrical parts of the encased motor which drives the pump. Such permeation can cause electrical failures, usually of the dielectric material of the motor. The reliability of continuously deflecting plastic/elastomer tubes in these peristaltic pumps also is open to question and gives concern that the tube might break and cause a lethal drug infusion into the body. An example of such peristaltic pumps is shown in Summer U.S. Pat. No. 3,527,220.

In order to overcome the efficiency and vapor permeation problems of peristaltic pumps, pulsatile pumps have more recently been employed to infuse liquid from a reservoir into the body. Examples of pulsatile pumps are shown in Ellingwood U.S. Pat. Nos. 3,923,060 and 4,146,029, and Thomas et al U.S. Pat. No. 3,963,380. These pulsatile pumps utilize check valves to prevent back flow into the reservoir and back flow of body fluids during the exhaust and intake strokes of the pumping cycle. In conventional larger size pumps, these check valves do not offer an unusual operational concern and can operate reliably. However, in ambulatory drug infusion devices these check valves are unusually small and must operate and seal at very low pressures with minuscule forces. For example, for an inlet check valve of 0.030 inches seat diameter, which is set to open at 2 psi differential, the spring load is only 0.001 pounds. Since some drugs can create "sticking" of the check valve poppet on its seat, these check valves are the primary cause of mechanical failure in pulsatile pumping devices. Furthermore, in some check valve arrangements, the inlet check valve has a very short lift and a very slow closing time. For example, the inlet check valve may stroke open only 70 millionths of an inch and require more than ten milliseconds to close. Such valve action acts to strain particulates out of the liquid and many such valves leak when these particles are trapped between the poppet and seat of the check valve. Also, it is sometimes desireable in such check valve arrangements to use rigid (hard) seat and poppet materials to minimize system compliance and thus improve volumetric pumping efficiency. Such hard seat and poppet materials will not absorb contaminants and particulates strained out of the liquid, and a crushing or cutting action, which requires considerable pressure, is not available to prevent leakage caused by such contaminants and particulates. In addition, in pulsatile pumping arrangements the pump exhaust stroke timing is crucial and means must be incorporated to delay the exhaust stroke until after the inlet check valve closes.

SUMMARY OF THE INVENTION

It is an object of the present invention to provide a new and improved medication infusion apparatus which avoids one or more of the difficulties of the above described prior art arrangements. Specifically, it is an object of the present invention to provide a medication infusion apparatus which is of the pulsatile pump type and eliminates all check valves so that the apparatus avoids the unreliability and life deficiencies of such prior art devices.

Briefly, in accordance with the present invention an integral valve and pumping unit is provided which employs only one moving part. This pumping unit is connected to the medication supply reservoir through a first flow restriction device which has directional flow characteristics so that liquid medication can flow readily from the reservoir to the pumping unit but liquid flow from the pumping unit to the reservoir encounters a relatively high resistance to flow in this device.

A second flow restriction device is connected between the pumping unit and the outlet catheter which is employed to infuse the medication into the body, this second flow restriction device likewise offering relatively little resistance to liquid flow from the pumping unit to the catheter while having relatively high resistance to flow in the opposite direction. Preferably, both of these flow restriction devices are vortex style fluidic flow resistance devices which have no moving parts, so that there is no possibility that these flow restriction devices may interfere with the operation of the pumping unit. At the same time, the valve portion of the integral valve-pump unit insures that there can be no flow of liquid either from the reservoir to the catheter, or vice versa, when the pumping unit is inoperative or when the reservoir is being filled.

DESCRIPTION OF THE DRAWINGS

The invention, both as to its organization and method of operation, together with further objects and advantages thereof, will best be understood by reference to the following specification taken in connection with the accompanying drawings in which:

FIG. 1 is a diagrammatic side elevational view of a medication infusion apparatus incorporating the features of the present invention;

FIGS. 2 and 3 are sectional views on a somewhat large scale, taken along lines 2—2 of 3—3 respectively of FIG. 1;

FIGS. 4 and 5 are schematic diagrams illustrating different ways of energizing the activating coil in the apparatus of FIG. 1; and FIG. 6 is a diagrammatic side elevational view of an alternative embodiment of the invention.

DETAILED DESCRIPTION OF THE INVENTION

Referring now to the drawings, the medication infusion apparatus of the present invention is therein illustrated as comprising an integral valve and pumping unit, indicated generally at 10, which is connected to a medication supply reservoir, indicated generally at 12, through a first directional flow restriction device, indicated generally at 14. The integral valve and pumping unit 10 is also connected to an outlet catheter, indicated generally at 16, through a second directional flow restriction device, indicated generally at 18. The integral valve and pumping unit 10 includes a coil 20 the energization of which is controlled by the control circuitry 22 which is energized from the battery 24. All of the components 10-24 may be contained within a housing 26 which may be implanted within a living body so that liquid medication, such as insulin, contained within the reservoir 12 may be infused into the body at a variable and programable rate by means of the catheter 16. In the alternative, all of these elements may be contained in an extracorporeal device, as will be described in more detail hereinafter.

Considering first the reservoir 12, this reservoir comprises a housing 30 in the top wall 32 of which is provided a septum 34. Preferably the housing 30 is made of metal for maximum structural reliability and so that the housing is leak proof to avoid permeation of the liquid medication into the body, this metal being chosen to be biocompatible with living tissue. A bellows 36 is provided within the housing 30 which has a movable end wall 38. The interior 40 of the bellows 36 is filled with a fluid which is in a two-phase (gas and liquid) state at the body temperature to maintain a pressure within the medication chamber 42 which is equal to or less than a chosen minimum body pressure. For example, this minimum body pressure may occur at the maximum earth ground altitude to be inhabited by the patient. Thus, the pressurant fluid within the bellows 36 may be filled at a pressure of 10.0 psig so that the pressure tending to expel medication from the chamber 42 will be less than body pressure at an altitude of 10,000 feet, i.e. 10.1 psi.

The septum 34 is made of a bio-compatible elastomer. The housing 26 is implanted in the body so that the septum 34 is located immediately below the surface of the skin. The medication reservoir 42 may then be refilled with a syringe by penetrating the skin and flesh layer and then through the septum until the syringe needle contacts a needle stop 44 attached to the top wall 32 of the housing 30. After the medication chamber 42 has been filled, the needle is withdrawn and the septum 34 self-seals. Initially, the medication chamber 42 is filled before implantation using a vacuum filling procedure to eliminate all air bubbles. A check valve or combination of check valves can also be used to redundantly seal the septum 34, if desired.

Considering now the directional flow restriction device 14, this device comprises a housing 50 in the form of a flat cylinder which has an inlet 52 extending perpendicularly away from the center of one sidewall 54 of the housing 50 (FIG. 2) and an outlet 56 communicating tangentially with the curved end wall 58 of the housing, as best illustrated in FIG. 1. When liquid is forced from the inlet 52 to the outlet 56 relatively little resistance to flow is experienced because this liquid flows directly from the inlet 52 to the outlet 56 as indicated by the arrow 60 in FIG. 2. However, when liquid attempts to flow from the outlet 56 to the inlet 50 it flows in a spiral pattern, as indicated by the arrow 62 in FIG. 2, and a substantial resistance to flow is experienced in this direction. This resistance to flow from outlet to inlet is caused by the shock losses of the constantly changing velocity as the tangentially introduced liquid flows in a decreasing radius path to the central outlet, and also by the friction losses between the adjacent liquid flow sections which are of different velocities and between the liquid flow and the liquid containing walls of device 14, so that a substantially greater resistance to flow in the direction from the outlet 56 to the inlet 52 is provided. Preferably, a ratio of approximately eight to one in flow resistance in the two directions is provided by the device 14 without employing any moving parts which can malfunction.

The device 18 is constructed similarly to the device 14 and provides relatively low resistance to the flow of liquid from the inlet 64 to the outlet 66 over the path indicated by the arrow 68 (FIG. 3). On the other hand, the flow of liquid from the outlet 66 to the inlet 64 again takes a spiral vortex path which provides substantial resistance to flow in this direction.

Considering now the integral valve and pumping unit 10, this unit comprises a housing 70 of magnetic material within which the coil 20 is positioned. A central leg 72, which is formed integrally with the housing 70, acts together with the top wall 74 and annular sidewalls 76 of the housing 70 to provide a core structure for the coil 20. This core structure is completed by a flat disc armature 78 which is movably mounted within the housing 70 by means of a diaphragm 80. A bipolar electromagnetic structure (solenoid) is thereby provided and when the coil 20 is energized the armature 78 is attracted upwardly until it strikes the shoulder portion 82 formed in the housing 70.

The diaphragm 80 and the central portion of the armature 78 form a movable sidewall portion of a pumping chamber 84 provided within the housing 70, the pumping chamber 84 communicating with the outlet 56 of the flow restriction device 14 at 86. An annular valve seat 88 is formed in the bottom wall 90 of the housing 70 at the center of the pumping chamber 84, the valve seat 88 being closed by a poppet valve element 92 which is carried by and positioned within a downwardly extending central boss portion 94 of the armature 78. The central bore 96 of the valve seat 88 communicates with the inlet 64 of the directional flow restriction device 18 through the conduit 98. The outer edge of the diaphragm 80 is secured to the outer wall 76 of the housing 70 and the inner edge of this diaphragm is secured to the boss portion 94 of the armature 78 so that the center of the diaphragm 80 and armature 78 move as an integral unit. In this connection it will be understood that a bellows or other suitable flexible member or possibly a sliding piston and seal arrangement may be used in place of the diaphragm 80 to form a portion of the movable wall of the pumping chamber 84 insofar as the present invention is concerned.

Considering now the operation of the integral valve and pumping unit, when the coil 20 is energized by the control circuitry 22, the armature 78 is lifted upwardly against the stop 82 and the diaphragm 80 moves therewith so as to increase the volume of the pumping chamber 84 and lift the poppet valve 92 off of the seat 88. This reduces the pressure in the pumping chamber 84 below the pressure in the reservoir chamber 42 since the system is completely filled with liquid. Accordingly, when the coil 20 is energized and the diaphragm 80 is lifted upwardly, liquid medication is drawn from the reservoir chamber 42 through the flow restriction device 14 in the low resistance direction of this device into the pumping chamber 84. A much smaller amount of liquid is drawn into the pumping chamber 84 from the outlet catheter 16 when the poppet valve 92 is lifted upwardly, because of the much higher resistance to fluid flow of the outlet flow restriction device 18 in this direction.

When the coil 20 is de-energized the mechanical spring force of the deflected diaphragm 80 returns the diaphragm to its initial position and seats the poppet valve 92 on the seat 88. As the poppet 92 returns to the seat 88 the pressure in the pumping chamber 84 is increased above the catheter outlet pressure, i.e., body pressure, and liquid medication is expelled through the outlet flow restriction device 18 in the low resistance direction thereof and out of the catheter 16 into the body. A much smaller quantity of liquid is returned to the reservoir as the diaphragm 80 returns to its initial position due to the much higher resistance to fluid flow of the inlet flow restriction device 14 in this direction.

When the poppet valve 92 is seated on the valve seat 88 it prevents back flow from the catheter 16 back to the reservoir chamber 42, even though body pressure may exceed reservoir pressure by a substantial amount. This permits the reservoir pressure within the chamber 42 to be set at a relatively low value relative to body pressure at sea level so that the reservoir pressure may be maintained below body pressure when the person in whose body the device is implanted travels to a much higher altitude and his body pressure will be substantially less, so that the pressure within the reservoir chamber 42 is maintained at all times below body pressure with the resultant advantages discussed in detail heretofore. Furthermore, the seating load with which the poppet valve 92 is urged against the seat 88 by the diaphragm 80 is many times greater than that possible with a simple spring loaded check valve. This high seating load tends to provide for absorption of contaminants in the relatively soft poppet 92 so that leakage through the valve by the collection of contaminants on the valve seat is avoided. Furthermore, the force which is available to overcome sticking of the poppet valve 92 on the seat 88 when the valve is opened is much greater with the electromagnetic armature arrangement of the present invention than with a conventional spring biased check valve.

Since the poppet valve 92 remains seated on the valve seat 88 at all times when the coil 20 is not energized this valve also prevents liquid medication from passing into the body when the medication reservoir chamber 42 is being refilled.

The volumetric efficiency of the integral valve in pumping unit 10 is a function of the system compliance characteristics, reservoir pressure relative to body pressure and the resistances of the inlet and outlet devices 14, 18 in their high resistance directions. The unit 10 has the highest efficiency when the body pressure approaches or equals the pressure within the reservoir 42 and when the devices 14, 18 have a high ratio of the resistance to flow in the high resistance as compared to the resistance to flow in the low resistance direction.

While the arrangement of FIG. 1 is one in which the valve seat 88 is associated with the outlet from the pumping chamber, it will be understood that this valve seat may equally as well be associated with the inlet flange 56, as shown in FIG. 6. Referring to this figure the valve seat 88a is provided at the end of the inlet conduit 56a on which the valve element 92a is seated by the force exerted by the diaphragm 80a. The pumping chamber 84a is provided with an outlet connected to the outlet conduit 64a which leads to the flow device 18. In other respects, the arrangement of FIG. 6 is identical to that of FIG. 1 described in detail heretofore. When the coil 20 is pulsed the armature 78 is moved upwardly to lift the valve element 92a off of the seat 88a to that indication can flow into the pumping chamber 84a as its volume increases. When the pulse of current through the coil terminates, the diaphragm returns the valve element 92a to the seat 88a as indication is forced out of the outlet 64a. The flow restrictive devices 14 and 18 function in the manner described, heretofore to limit flow from the inlet 56a to the reservoir 12 and from the catheter 16 to the outlet 64a.

In accordance with an important aspect of the invention, the integral valve and pumping unit 10 and the directional flow control devices 14 and 18 may be made very small so that the housing 26 can be of relatively small overall dimensions for ease in inplanting within the body or to facilitate the provision of an external device of relatively small dimensions. The integral valve and pumping unit 10 may have a diameter of seven eighths of an inch and a thickness of one-half inch. The fluid control devices 14 and 18 may be of 0.25 inches diameter and 0.10 inches in thickness. In this connection, it will be understood that these elements are not shown to scale in the drawings, for purposes of clarity of description thereof.

By providing an integral valve and pumping unit which can be made with such extremely small dimensions, the arrangement of the present invention has the further advantage that an extremely small amount of power is required to energize the coil 20 at predetermined periods to provide a desired flow rate, so that the current demand on the battery 24 is minimized with the result that it may remain in the body for a considerable period of time before it needs to be replaced. For example, the the control circuitry 22 may be arranged to supply a pulse of current to the coil every six seconds and the integral valve pump unit 10 responds to each such current pulse by pumping one microliter, for example, of medication from the reservoir 40 to the catheter 16. The coil 20 may comprise 100 turns of AWG No. 28 wire so that only approximately one milliwatt-second of energy is required to dispense one microliter of medication. It is, therefore, possible with the arrangement of the present invention to provide a controllable, very minute pulsatile flow of medication to the body over long periods of time. Furthermore, the control circuitry 22 may include suitable programming facilities for varying the rate at which pulses are applied to the coil 20 and hence varying the rate at which medication is infused into the body, as will be readily understood by those skilled in the art.

In FIG. 3 a circuit arrangement is shown wherein the battery 24 is employed directly to supply a pulse of current to the coil 20. Referring to this figure, the battery 24 is connected directly to the coil 20 through the switch 96, a diode 98 being connected across the coil to prolong the current pulse through the coil 20. Preferably, the switch 96 is a solid state device which is controlled by a suitable timing device, such as an oscillator, in the control circuitry 22.

In the alternative, the preferred circuit arrangement shown in FIG. 4 may be employed to energize the coil 20 from the battery 24. Referring to this figure, a capacitor 100 is arranged to be charged from the battery 24 through a single pole double throw switch 102 during the period between pumping cycles, ie. for six seconds. After the capacitor 100 has thus been charged, the switch 102 is thrown to the position which connects the capacitor 100 to the coil 20 so that the capacitor 100 is abruptly discharged and provides a pulse of current to the coil 20. This current pulse may be of relatively large magnitude without draining an excessive amount of current from the battery 24 because the capacitor 100 is charged from the battery 24 at a very slow rate over a long period of time and then is discharged abruptly in a very short period of time to provide a current pulse of the proper magnitude to actuate the armature 78 and provide the necessary pumping action. The switch 102 is also preferably a solid state device which is controlled by a suitable timing circuit in the control circuitry 22. In this connection, it will be understood that the control circuitry 22 may include a microprocessor which is energized from the battery 24 and includes suitable clock timing circuits to accomplish any desired programming of the valve and pumping unit 10.

While the apparatus of the present invention is particularly suitably for implanting within the body, it should be understood that the integral valve and pumping unit 10 and inlet and outlet fluidic restrictors 14 and 18 may also be employed in an external device which can be worn by ambulatory patients with subcutaneous or intravenous infusion into the body through the catheter 16. However, with such an externally located system, the reservoir including the housing 12 may be replaced by a simple bag which is made of an elastomer or plastic material and is filled with medication, this bag having an pressure reference equal to atmospheric pressure on the bag. This lower cost construction is satisfactory since bag leakage only disables the system temporarily until a replacement bag can be fitted, which is easily done in an externally located system. Since the pressure reference in the medication reservoir is ambient i.e., atmospheric pressure and since body pressure is nearly the same as ambient pressure, the externally positioned system always operates at the same volumetric efficiency which is also nearly optimum.

While there have been illustrated and described various embodiments of the present invention, it will be apparent that various changes and modifications thereof will occur to those skilled in the art. It is intended in the appended claims to cover all such changes and modifications as fall within the true spirit and scope of the present invention.

What is claimed as new and desired to be secured by Letters Patent of the United States is:

1. In a system for infusing medication into the body, the combination of, a reservoir of medication, a pumping chamber, a medication outlet, a first flow control device connected between said reservoir and said pumping chamber which permits liquid to flow in both directions between said pumping chamber and said reservoir but offers substantially less resistance to liquid flow from said reservoir to said pumping chamber than for liquid flow from said pumping chamber to said reservoir, a second flow control device connected between said pumping chamber and said outlet which permits liquid to flow in both directions between said pumping chamber and said outlet but offers substantially less resistance to liquid flow from said pumping chamber to said outlet than for liquid flow from said outlet to said pumping chamber, means for increasing the volume of said pumping chamber so that liquid flows primarily from said reservoir to said pumping chamber through said first flow control device, and means for decreasing the volume of said pumping chamber so that fluid flows primarily from said pumping chamber to said outlet through said second flow control device.

2. The combination of claim 1, wherein said means for increasing the volume of said pumping chamber comprises a movable member forming a wall portion of said pumping chamber, an armature connected to said movable member, and electromagnetic means for attracting said armature so that said movable member is moved in the direction to increase the volume of said pumping chamber.

3. The combination of claim 2, wherein said movable member is a flexible member which is connected to said armature so that the volume of said pumping chamber is increased when said armature is attracted by said electromagnetic means, and means acting to return said armature to its initial position when said armature is no longer attracted by said electromagnetic means, thereby to decrease the volume of said pumping chamber.

4. The combination of claim 3, which includes means defining a valve seat in said pumping chamber and communicating with said outlet, and a valve element movable with said movable member and seated on said valve seat when said flexible member is in said initial position, said valve element being lifted off of said valve seat when said flexible member is moved to increase the volume of said pumping chamber.

5. The combination of claim 3, which includes means defining a valve seat in said pumping chamber and communicating with said reservoir and a valve element movable with said movable member and seated on said valve seat when said flexible member is in said initial position, said valve element being lifted off of said valve seat when said flexible member is moved to increase tne volume of said pumping chamber.

6. In a system for infusing liquid into a living body, an infusate reservoir, an infusate outlet, a movably mounted armature of magnetic material, means defining a pumping chamber having a movable wall portion connected to said armature, electromagnetic means for moving said armature so that the volume of said pumping chamber is altered, means defining a valve seat in said pumping chamber and communicating with said infusate outlet, a valve element connected to and movable with said movable wall portion and arranged to be seated on said valve seat, a first directional flow control device connected between said infusate reservoir and said pumping chamber and offering minimum resistance to flow of infusate from said reservoir to said pumping chamber, and a second directional flow control device connected between said pumping chamber and said infusate outlet and offering minimum resistance to flow to infusate from said pumping chamber to said outlet.

7. In a system for infusing liquid into a living body, an infusate reservoir, means defining a pumping chamber, an infusate outlet, a movably mounted armature of magnetic material, means defining a pumping chamber having a movable wall portion connected to said armature so that the volume of said pumping chamber is altered, means defining a valve seat in said pumping chamber and communicating with said infusate outlet, a valve element connected to and movable with said movable wall portion and arranged to be seated on said valve seat, and a directional flow control device connected between said pumping chamber and said infusate outlet and offering minimum resistance to flow to infusate from said pumping chamber to said outlet.

8. A combined valve actuator and pumping unit for use in a system for dispensing medication into the body, comprising a magnetic core, a coil mounted on said core, armature means arranged to complete a magnetic flux path with said core and moved in response to energization of said coil, means defining a pumping chamber including a movable wall portion connected to said armature means for movement therewith, a medication inlet to said pumping chamber, a medication catheter outlet, means defining a valve seat in said pumping chamber and communicating with said outlet, and a valve element connected to and movable with said movable wall portion and seated on said valve seat when said coil is de-energized, said movable wall portion moving in a direction to increase the volume of said pumping chamber in response to movement of said armature means when said coil is energized while at the same time lifting said valve element off of said valve seat.

9. An integral valve and pumping unit as set forth in claim 8, which includes a support on which said armature means is movably mounted, and said movable wall portion includes a flexible diaphragm connected at its outer edges to said support and connected to said armature means in the central region thereof.

10. An integral valve and pumping unit as set forth in claim 9, wherein said diaphragm is of the single convoluted type.

11. A combined valve actuator and pumping unit for use in a system for dispensing medication into the body, comprising a magnetic core, a coil mounted on said core, armature means arranged to complete a magnetic flux path with said core and moved in response to energization of said coil, a support on which said armature means is movable mounted, said armature means comprising a flat disc having a raised central portion, means defining a pumping chamber including a movable wall portion comprising a flexible diaphragm extending generally parallel to the flat plane of said disc and connected at its outer edges to said support, means connecting said diaphragm to said raised central portion of said armature disc, a medication inlet to said pumping chamber, a medication catheter outlet, means defining a valve seat in said pumping chamber and communicating with said outlet, and a valve element movable with said diaphragm and seated on said valve seat when said coil is de-energized, said diaphragm moving in a direction to increase the volume of said pumping chamber in response to movement of said armature means when said coil is energized while at the same time lifting said valve element off of said valve seat.

12. An integral valve and pumping unit as set forth in claim 11, wherein said raised central portion of said armature disc is in the form of an annular shoulder and said diaphragm is connected to said annular shoulder.

13. An integral valve and pumping unit as set forth in claim 12, which includes a valve insert of resilient material positioned on said armature disc within said annular shoulder and adapted to engage said valve seat and close said outlet.

14. A combined valve actuator and pumping unit for use in a system for dispensing medication into the body, comprising a magnetic core, a coil mounted on said core, armature means arranged to complete a magnetic flux path with said core and moved in response to energization of said coil, means defining a pumping chamber including a movable wall portion connected to said armature means for movement therewith, a medication inlet to said pumping chamber, a medication catheter outlet, means defining a valve seat in said pumping chamber and communicating with said inlet, and a valve element connected to and movable with said movable wall portion and seated on said valve seat when said coil is de-energized, said movable wall portion moving in a direction to increase the volume of said pumping chamber in response to movement of said armature means when said coil is energized while at the same time lifting said valve element off of said valve seat.

15. An integral valve and pumping unit as set forth in claim 8, which includes a support on which said armature means is movably mounted, and said movable wall portion includes a flexible member connected to said support.

16. An integral valve and pumping unit as set forth in claim 14, wherein said flexible member is a diaphragm of the single convoluted type connected at its outer edges to said support and connected to said armature means in the central region thereof.

17. A combined valve actuator and pumping unit for use in a system for dispensing medication into the body, comprising a magnetic core, a coil mounted on said core, armature means arranged to complete a magnetic flux path with said core and moved in response to energization of said coil, a support on which said armature means is movably mounted, said armature means comprising a flat disc having a raised central portion, means defining a pumping chamber including a movable wall portion comprising a flexible member connected to said support and to said raised central portion of said armature disc, a medication inlet to said pumping chamber, a medication catheter outlet, means defining a valve seat in said pumping chamber and communicating with said inlet, and a valve element movable with said flexible member and seated on said valve seat when said coil is de-energized, said flexible member moving in a direction to increase the volume of said pumping chamber in response to movement of said armature means when said coil is energized while at the same time lifting said valve element off of said valve seat.

18. The combination of claim 1, which includes a magnetic core, a coil mounted on said core, armature means arranged to complete a magnetic flux path with said core and moved in response to energization of said coil, said pumping chamber having a movable wall portion connected to said armature means for movement therewith, means defining a valve seat, a valve element movable with said movable wall portion and seated on said valve seat when said coil is de-energized, said movable wall portion moving in a direction to increase the volume of said pumping chamber and lift said valve element off of said valve seat when said coil is energized.

19. The combination of claim 18, which includes a support on which said armature means is movably mounted, and said movable wall portion includes a flexible member connected between said support and said armature means.

20. The combination of claim 18, which includes a housing within which said armature means is movably mounted, and said armature means comprising a flat disc having a raised central portion and said movable wall portion comprising a flexible diaphragm extending generally parallel to the flat plane of said disc and connected at its outer edges to said housing, and means connecting said diaphragm to said raised central portion of said armature disc.

21. The combination of claim 20, wherein said raised central portion of said armature disc is in the form of an annular shoulder and said diaphragm is connected to said annular shoulder.

22. The combination of claim 21, which includes a valve insert of resilient material positioned on said armature disc within said annular shoulder and adapted to engage said valve seat when said coil is de-energized.

23. The arrangement of claim 8, which includes a medication reservoir, and a flow control device connected between said reservoir and said medication inlet, said flow control device permitting medication to flow in both directions between said reservoir and said pumping chamber but offering substantially less resistance to flow of medication from said reservoir to said pumping chamber than for flow of medication from said pumping chamber to said reservoir.

24. A combined valve actuator and pumping unit for use in a system for dispensing medication into the body, comprising a magnetic core, a coil mounted on said core, armature means arranged to complete a magnetic flux path with said core and moved in response to energization of said coil, means defining a pumping chamber including a movable wall portion connected to said armature means for movement therewith, a medication inlet to said pumping chamber, a medication reservoir, a flow control device connected between said reservoir and said medication inlet, said flow control device permitting medication to flow in both directions between said reservoir and said pumping chamber but offering substantially less resistance to flow of medication from said reservoir to said pumping chamber than for flow of medication from said pumping chamber to said reservoir, said flow control device being a vortex type device in which medication is forced to flow in a decreasing spiral from said pumping chamber to said reservoir, a medictaion catheter outlet, means defining a valve seat in said pumping chamber and communicating with said outlet, and a valve element movable with said movable wall portion and seated on said valve seat when said coil is de-energized, said movable wall portion moving in a direction to increase the volume of said pumping chamber in response to movement of said armature means when said coil is energized while at the same time lifting said valve element off of said valve seat.

25. A combined valve actuator and pumping unit for use in a system for dispensing medication into the body, comprising a magnetic core, a coil mounted on said core, armature means arranged to complete a magnetic flux path with said core and moved in response to energization of said coil, means defining a pumping chamber including a movable wall portion connected to said armature means for movement therewith, a medication inlet to said pumping chamber, a medication reservoir, a flow control device connected between said reservoir and said medication inlet, said flow control device permitting medication to flow in both directions between said reservoir and said pumping chamber but offering substantially less resistance to flow of medication from said reservoir to said pumping chamber than for flow of medication from said pumping chamber to said reservoir, the ratio of resistance to flow from pumping chamber to reservoir to resistance to flow from reservoir to pumping chamber of said flow control device being in the order of 8 to 1, a medication catheter outlet, means defining a valve seat in said pumping chamber and communicating with said outlet, and a valve element movable with said movable wall portion and seated on said valve seat when said coil is de-energized, said movable wall portion moving in a direction to increase the volume of said pumping chamber in response to movement of said armature means when said coil is energized while at the same time lifting said valve element off of said valve seat.

26. A combined valve actuator and pumping unit for use in a system for dispensing medication into the body, comprising a magnetic core, a coil mounted on said core, armature means arranged to complete a magnetic flux path with said core and moved in response to energization of said coil, means defining a pumping chamber including a movable wall portion connected to said armature means for movement therewith, a medication inlet to said pumping chamber, a medication catheter outlet, means defining a valve seat in said pumping chamber and communicating with said outlet, and a value element movable with said movable wall portion and seated on said valve seat when said coil is de-energized, said movable wall portion moving in a direction to increase the volume of said pumping chamber in response to movement of said armature means when said coil is energized while at the same time lifting said valve element off of said valve seat and a flow control device connected between said pumping chamber and said medication outlet, said flow control device permitting medication to flow in both directions between said outlet and said pumping chamber but offering substantially less resistance to flow of medication from said pumping chamber to said outlet than for flow of medication from said outlet to said pumping chamber.

27. The arrangement of claim 26, wherein said flow control device is a vortex type device in which medication is forced to flow in a decreasing spiral from said outlet to said pumping chamber.

28. The arrangement of claim 26, wherein the ratio of resistance to flow from pumping chamber to outlet to resistance to flow from outlet to pumping chamber of said flow control device is in the order of 1 to 8.

29. The arrangement of claim 8, which includes a medication reservoir, and a directional flow control device connected between said reservoir and said inlet, said device having no moving parts but offering substantially less resistance to flow of medication from said reservoir to said pumping chamber than for flow of medication from said pumping chamber to said reservoir.

30. A combined valve actuator and pumping unit for use in a system for dispensing medication into the body, comprising a magnetic core, a coil mounted on said core, armature means arranged to complete a magnetic flux path with said core and moved in response to energization of said coil, means defining a pumping chamber including a movable wall portion connected to said armature means for movement therewith, a medication inlet to said pumping chamber, a medication reservoir, a directional flow control device connected between said reservoir and said inlet, said device having no moving parts but offering substantially less resistance to flow of medication from said reservoir to said pumping chamber than for flow of medication from said pumping chamber to said reservoir, the ratio of resistance to flow from pumping chamber to reservoir to resistance to flow from reservoir to pumping chamber of said flow control device being in the order of 8 to 1 a medication catheter outlet, means defining a valve seat in said pumping chamber and communicating with said outlet, and a valve element movable with said movable wall portion and seated on said valve seat when said coil is de-energized, said movable wall portion moving in a direction to increase the volume of said pumping chamber in response to movement of said armature means when said coil is energized while at the same time lifting said valve element off of said valve seat.

31. A combined valve actuator and pumping unit for use in a system for dispensing medication into the body, comprising a magnetic core, a coil mounted on said core, armature means arranged to complete a magnetic flux path with said core and moved in response to energization of said coil, means defining a pumping chamber including a movable wall portion connected to said armature means for movement therewith, a medication inlet to said pumping chamber, a medication catheter outlet, means defining a valve seat in said pumping chamber and communicating with said outlet, and a valve element movable with said movable wall portion and seated on said valve seat when said coil is de-energized, said movable wall portion moving in a direction to increase the volume of said pumping chamber in response to movement of said armature means when said coil is energized while at the same time lifting said valve element off of said valve seat, and a directional flow control device connected between said pumping chamber and said outlet, said device having no moving parts but offering substantially less resistance to flow of medication from said pumping chamber to said outlet than for flow of medication from said outlet to said pumping chamber.

32. The arrangement of claim 31, wherein the ratio of resistance to flow from outlet to pumping chamber to resistance to flow from pumping chamber to outlet of said flow control device is in the order of 8 to 1.

33. The arrangement of claim 14, which includes a medication reservoir, and a directional flow control device connected between said reservoir and said inlet, said device having no moving parts but offering substantially less resistance to flow of medication from said reservoir to said pumping chamber than for flow of medication from said pumping chamber to said reservoir.

34. A combined valve actuator and pumping unit for use in a system for dispensing medication into the body, comprising a magnetic core, a coil mounted on said core, armature means arranged to complete a magnetic flux path with said core and moved in response to energization of said coil, means defining a pumping chamber including a movable wall portion connected to said armature means for movement therewith, a medication inlet to said pumping chamber, a medication reservoir, a directional flow control device connected between said reservoir and said inlet, said device having no moving parts but offering substantailly less resistance to flow of medication from said reservoir to said pumping chamber than for flow of medication from said pumping chamber to said reservoir, the ratio of resistance to flow from pumping chamber to reservoir to resistance to flow from reservoir to pumping chamber of said flow control device is in the order of 8 to 1, a medication catheter outlet, means defining a valve seat in said pumping chamber and communicating with said inlet, and a valve element movable with said movable wall portion and seated on said valve seat when said coil is de-energized, said movable wall portion moving in a direction to increase the volume of said pumping chamber in response to movement of said armature means when said coil is energized while at the same time lifting said valve off of said valve seat.

35. A combined valve actuator and pumping unit for use in a system for dispensing medication into the body, comprising a magnetic core, a coil mounted on said core, armature means arranged to complete a magnetic flux path with said core and moved in response to energization of said coil, means defining a pumping chamber including a movable wall portion connected to said armature means for movement therewith, a medication inlet to said pumping chamber, a medication catheter outlet, a directional flow control device connected between said pumping chamber and said outlet, said device having no moving parts but offering substantially less resistance to flow of medication from said pumping chamber to said outlet than for flow of medication from said outlet to said pumping chamber, means defining a valve seat in said pumping chamber and communicating with said inlet, and a valve element movable with said movable wall portion and seated on said valve seat when said coil is de-energized, said movable wall portion moving in a direction to increase the volume of said pumping chamber in response to movement of said armature means when said coil is energized while at the same time lifting said valve element off of said valve seat.

36. The arragnement of claim 35 wherin the ratio of resistance to flow from outlet to pumping chamber to resistance to flow from pumping chamber to outlet of said flow control device is in the order of 8 to 1.

* * * * *